United States Patent [19]
Rubinfeld et al.

[11] Patent Number: 6,017,948
[45] Date of Patent: Jan. 25, 2000

[54] WATER-MISCIBLE PHARMACEUTICAL COMPOSITIONS

[75] Inventors: Joseph Rubinfeld, Danville; Ashok Y. Gore, San Ramon; Rajashree Joshi, Milpitas; Rajesh Shrotriya, Danville, all of Calif.

[73] Assignee: Supergen, Inc., San Ramon, Calif.

[21] Appl. No.: 09/183,199

[22] Filed: Oct. 30, 1998

[51] Int. Cl.$^7$ ............................ A01N 37/06; A61K 31/22
[52] U.S. Cl. ...................... 514/449; 514/936; 514/937; 514/941; 514/943; 514/922; 514/970; 514/974
[58] Field of Search .................................. 514/449, 936, 514/937, 941, 943, 922, 970, 974

[56] References Cited

U.S. PATENT DOCUMENTS

| | | | |
|---|---|---|---|
| 4,772,589 | 9/1988 | Kaplan et al. | 514/33 |
| 5,034,397 | 7/1991 | Kaplan et al. | 514/297 |
| 5,082,863 | 1/1992 | Apelian et al. | 514/618 |
| 5,504,102 | 4/1996 | Agharkar et al. | 514/449 |
| 5,641,803 | 6/1997 | Carretta et al. | 514/449 |
| 5,670,537 | 9/1997 | Canetta et al. | 514/449 |
| 5,681,846 | 10/1997 | Trissel | 514/449 |
| 5,726,181 | 3/1998 | Hausheer et al. | 514/283 |
| 5,877,205 | 3/1999 | Andersson | 514/449 |

FOREIGN PATENT DOCUMENTS

| | | |
|---|---|---|
| 905528 | 2/1987 | Belgium . |
| 0 626 171 A1 | 5/1993 | European Pat. Off. . |
| 0645145B1 | 3/1997 | European Pat. Off. . |
| WO 90/14094 | 11/1990 | WIPO . |
| WO 96/06618 | 3/1996 | WIPO . |
| WO 96/21427 | 7/1996 | WIPO . |
| WO 96/39143 | 12/1996 | WIPO . |
| WO 97/23217 | 7/1997 | WIPO . |
| WO 97/26895 | 7/1997 | WIPO . |

OTHER PUBLICATIONS

R. Pfeifer et al., "Precipitation of paclitaxel during infusion by pump", *Am J Hosp Pharm*, 50 (Dec. 1993).

D. Rischin et al., "Cremophor Pharmacolinetics in Patients Receiving 3–, 6–, and 24–Hour Infusions of Paclitaxel", *J. of the National Cancer Institute*, 88:18 (Sep. 18, 1996).

M. Markman et al., "Intraperitoneal Paclitaxel: A Possible Role in the Management of Ovarian Cancer?", *Seminars in Oncology*, 22:3(6), 84–87 (Jun. 1995).

J. Adams et al., "Taxol: A History of Pharmaceutical Development and Current Pharmaceutical Concerns", *J. of the National Cancer Institute Monographs*, 15 (1993).

A. Sparreboom et al., "Preclinical Pharmacokinetics of paclitaxel and docetaxel", *Anticancer Drugs*, 9(1): 1–17 (Jan. 1998).

SV Balasubramanian et al., "Taxol–lipid interactions: tax-ol–dependent effects on the physical properties of model membranes", *Biochemistry*, 33(30):8941–8947 (Aug. 1994).

BD Tarr et al., "A New Parenteral Emulsion for the Administration of Taxol", *Pharmaceutical Research*, 4:2 (1987).

*Primary Examiner*—Frederick Krass
*Attorney, Agent, or Firm*—David J. Weitz; Wilson Sonsini Goodrich & Rosati

[57] ABSTRACT

Disclosed are compositions comprising paclitaxel; and a pharmaceutically-acceptable, water-miscible, non-aqueous solvent, together with kits comprising the composition and methods of using the composition.

25 Claims, 1 Drawing Sheet

Effect of aqueous dilution on the viscosity of paclitaxel formulations

WATER-MISCIBLE PHARMACEUTICAL COMPOSITIONS

BACKGROUND OF THE INVENTION

1. Field of the Invention

This invention relates to compositions that may be used as pharmaceutical compositions, methods and kits, more particularly to improved pharmaceutical compositions, methods and kits including paclitaxel and pharmaceutically-acceptable, water-miscible, non-aqueous solvents.

2. Description of Related Art

Paclitaxel is a unique diterpene anticancer compound derived from the bark of the *Taxus brevifolia* (Pacific yew) tree. A crude extract of the bark demonstrated antineoplastic activity in preclinical tumor screening 30 years ago as part of the National Cancer Institute's (NCI's) large-scale screening program. The active component of the extract, paclitaxel, was isolated and described by M. C. Wani et al, *Plant antitumor agents. VI: The isolation and structure of Paclitaxel, a novel antileukemic and antitumor agent from Taxus brevifolia*, J. Am. Chem. Soc. 93:2325–2327 (1971). This document, and all others referred to herein, are incorporated by reference as if reproduced fully below.

In 1979, Schiff and coworkers rekindled interest in the development of paclitaxel by demonstrating its novel mechanism of action. Paclitaxel stabilizes the tubulin polymer and promotes microtubule assembly, rather than inducing microtubule disassembly like the antimicrotubule agents colchicine, vincristine, and vinblastine. This stabilization results in the inhibition of the normal dynamic reorganization of the microtubule network. Encouraging response rates (complete and partial) have been reported in single-agent phase II studies of paclitaxel in breast cancer, previously untreated non-small-cell lung cancer, head and neck cancer, and refractory ovarian cancer.

Unfortunately, paclitaxel is poorly soluble in water (less than 0.01 mg/mL) and other common vehicles used for the parenteral administration of drugs. Certain organic solvents, however, may at least partially dissolve paclitaxel. However, when a water-miscible organic solvent containing paclitaxel at near its saturation solubility is diluted with water, the drug may precipitate.

Solubilization of compounds with surfactants allows for dilution of saturated or near-saturated formulations. Consequently, researchers formulated paclitaxel formulations using 50% Cremophor EL/50% dehydrated alcohol, USP, diluted in NS or D5W to a final concentration of 5% Cremophor EL/5% dehydrated alcohol or less, for the intravenous administration of drug to humans in initial clinical trials. (Cremophor EL; Badische Anilin and Soda Fabrik AG [BASF], Ludwigshafen, Federal Republic of Germany). Paclitaxel for injection concentrate is currently available from Bristol-Myers Squibb Co. (New York, N.Y.) in 30-mg (5-mL) single-dose vials. Each milliliter of formulation contains approximately 6 mg Paclitaxel, 527 mg of Cremophor EL, and 49.7% (vol/vol) dehydrated alcohol. This concentrated formulation must be further diluted with NS, D5W, D5NS, or D5W-R prior to administration. Additional information regarding Cremophor formulations of paclitaxel may be found in Agharkar et al., U.S. Pat. No. 5,504,102.

An unexpectedly high incidence of serious hypersensitivity reactions was noted in phase I studies of the paclitaxel/Cremophor formulations. At least one patient's death was caused by an allergic reaction induced by the formulation. It is not clear whether the hypersensitivity reactions were related to the Cremophor EL vehicle or to the paclitaxel. D. M. Essayan et al., *Successful Parenteral Desensitization to Paclitaxel*, J. Allergy and Clin. Immun. 97:42–46 (1996). Studies have shown that the Cremophor EL vehicle induces histamine release and hypotension in dogs within 10 minutes of administration.

In January 1985, the NCI sent a letter to all phase I investigators using paclitaxel, directing them to increase the duration of paclitaxel infusions and to pretreat all subjects with antihistamines (both H, and H2 blockers) and steroids. The incidence of hypersensitivity reactions subsequently decreased. Because the infusion duration was increased and pretreatment medications were added at the same time, it was not possible to determine whether infusion rate or pretreatment was the important factor.

Further studies were carried out in which paclitaxel was administered after premedication with steroids (such as dexamethasone), antihistamines (such as diphenhydramine), and H2-antagonists (such as cimetidine or ranitidine), and the infusion time was extended to 24 hours in an attempt to eliminate the most serious allergic reactions. See Einzig, et al., *Phase II Trial of Taxol in Patients with Metastatic Renal Cell Carcinoma*, Cancer Investigation, 9:133–136 (1991); A. B. Miller et al., *Reporting Results of Cancer Treatment*, Cancer 47:207–214 (1981). Additional description of premedication techniques may be found in Carretta et al., U.S. Pat. No. 5,670,537.

Although use of a long infusion duration seems to reduce the occurrence of hypersensitivity reactions, the long infusion duration is inconvenient for patients, and is expensive due to the need to monitor the patients for the entire 6 to 24-hour infusion duration; further, the long infusion duration requires that patients spend at least one night in a hospital or treatment clinic. The desire to reduce the cost and inconvenience led to shortened infusion regimes. Such shortened infusions are described in Carretta et al., U.S. Pat. No. 5,641,803.

However, these shortened infusion regimes still require the use of pretreatment, which is expensive and taxing for the patient. Additionally, even for shortened infusion times, paclitaxel is still administered in a Cremophor-containing formulation that is believed by many clinicians to promote hypersensitivity reactions in certain patients despite pretreatment.

There are other disadvantages to using Cremophor formulations as well. Polyvinylchloride (PVC) infusion bags and intravenous administration sets usually contain diethylhexylphthalate (DEHP) as a plasticizer to maximize component flexibility. DEHP leaches to some extent into aqueous infusion fluids and blood products that come in contact with PVC materials. Exposure of animals to chronic high doses (more than 100 mg/kg) of DEHP has resulted in toxic effects including growth retardation, liver weight increase, liver damage, testicular atrophy, teratogenicity, and carcinogenicity. Cosolvents and surfactants may increase the amount of plasticizer leached. Waugh and colleagues evaluated the quantities of DEHP extracted from PVC infusion devices by the commercially available paclitaxel formulation. Substantial quantities of DEHP were extracted by all formulation concentrations tested. Therefore, there is a substantial health risk to patients receiving paclitaxel in the commercially available formulation using conventional PVC-containing equipment. While the danger can be ameliorated by using different materials for the equipment, this is not a complete solution.

There is therefore a need for improved formulations comprising paclitaxel, methods of treatment using these formulation and kits comprising these formulations, to overcome the problems of conventional paclitaxel formulations as noted above and as known to one of skill in the art.

SUMMARY OF THE INVENTION

In an aspect, the invention relates to a composition comprising: paclitaxel; and a pharmaceutically-acceptable, water-miscible, non-aqueous solvent; wherein the composition is suitable for administration to a host in need thereof, and wherein the composition has a concentration of paclitaxel greater than or equal to about 1.5 mg/mL, a viscosity less than or equal to about 3.0 cp, as determined by the pipette/capillary method, and is substantially stable for four weeks at 50° C.; and wherein the pharmaceutically-acceptable, water-miscible, non-aqueous solvent has an average LD50, when administered intravenously to a mouse, of greater than or equal to about 2.0 mL/kg.

In another aspect, the invention relates to a composition made by the acts comprising providing paclitaxel; combining the paclitaxel with a pharmaceutically-acceptable, water-miscible, non-aqueous solvent; wherein the composition is suitable for administration to a host in need thereof, and wherein the composition has a concentration of paclitaxel greater than or equal to about 1.5 mg/mL, a viscosity less than or equal to about 3.0 cp, as determined by the pipette/capillary method, and is substantially stable for four weeks at fifty degrees Celsius; and wherein the pharmaceutically-acceptable, water-miscible, non-aqueous solvent has an average LD50, when administered intravenously to a mouse, of greater than or equal to about 2.0 mL/kg.

In another aspect, the invention relates to a composition comprising: paclitaxel; and a pharmaceutically-acceptable, water-miscible, non-aqueous solvent; wherein the composition is substantially ethanol-free.

In still another aspect, the invention relates to a composition made by the acts comprising: providing paclitaxel; combining the paclitaxel with a pharmaceutically-acceptable, water-miscible, non-aqueous solvent; wherein the composition is substantially ethanol-free.

In a further aspect, the invention relates to a composition comprising: paclitaxel; and a pharmaceutically-acceptable, water-miscible, non-aqueous solvent; wherein the pharmaceutically-acceptable, water-miscible, non-aqueous solvent comprises N-methol-2-pyrrolidone, 2-pyrrolidone, dimethyl sulfoxide, propylene glycol, benzyl alcohol, ethyl acetate, or dimethylacetamide.

In another aspect, the invention relates to a composition made by the acts comprising: providing paclitaxel; combining the paclitaxel with a pharmaceutically-acceptable, water-miscible, non-aqueous solvent; wherein the pharmaceutically-acceptable, water-miscible, non-aqueous solvent comprises N-methol-2-pyrrolidone, 2-pyrrolidone, dimethyl sulfoxide, propylene glycol, benzyl alcohol, ethyl acetate, or dimethylacetamide.

DETAILED DESCRIPTION OF THE INVENTION

Figure 1:
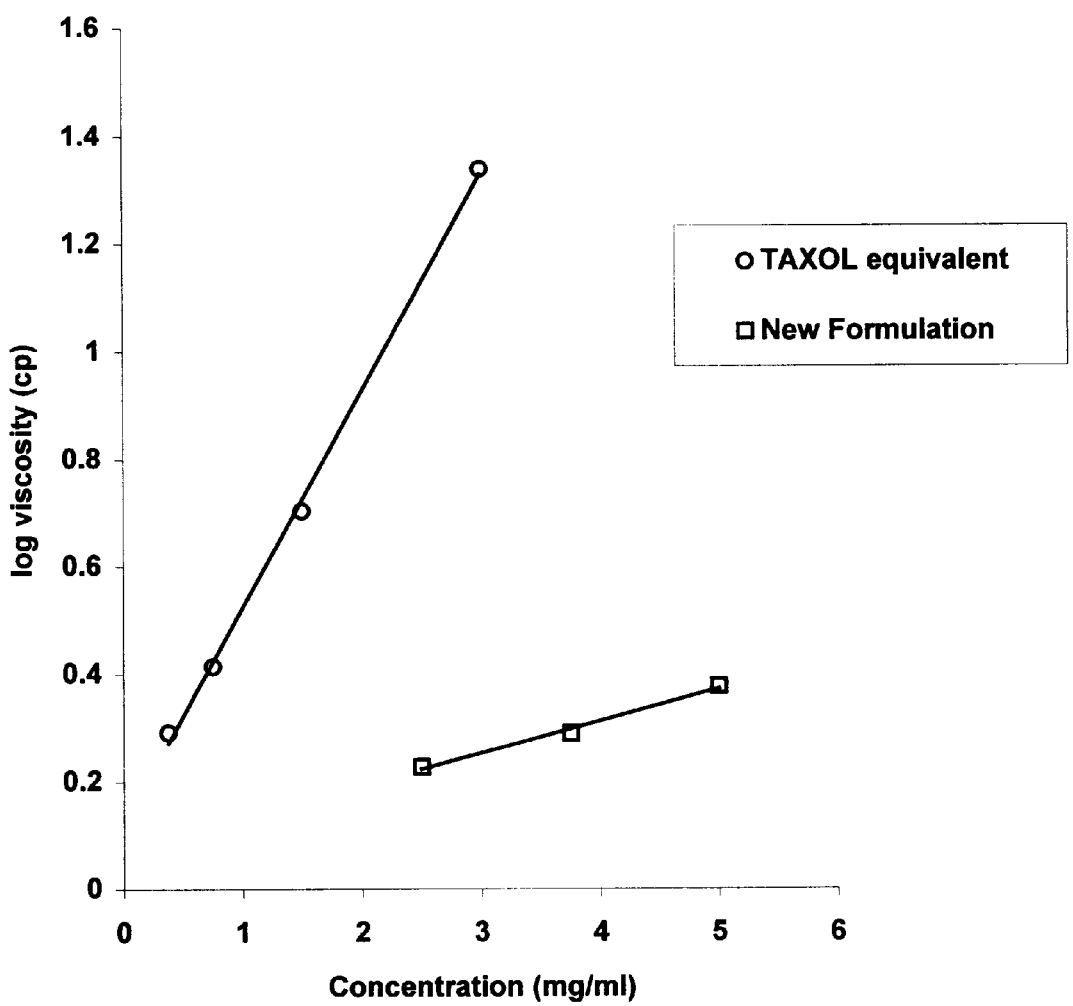
FIG. 1 is a graph showing the effect of aqueous dilution on the viscosity of paclitaxel formulations.

The inventors have unexpectedly and surprisingly discovered that it is possible to use certain pharmaceutically-acceptable, water-miscible, non-aqueous solvents, or pharmaceutically-acceptable, water-miscible, non-aqueous solvents under certain conditions to arrive at compositions comprising paclitaxel (abbreviated as "PCT" on occasion) and these solvents. These compositions offer the possibility of overcoming the problems of conventional, Cremophor-containing paclitaxel formulations. Such inventive compositions are described in more detail below.

In an aspect, the invention relates to a composition comprising: paclitaxel; and a pharmaceutically-acceptable, water-miscible, non-aqueous solvent; wherein the composition is suitable for administration to a host in need thereof, and wherein the composition has a concentration of paclitaxel greater than or equal to about 1.5 mg/mL, a viscosity less than or equal to about 3.0 cp, as determined by the pipette/capillary method, and is substantially stable for four weeks at 50° C.; and wherein the pharmaceutically-acceptable, water-miscible, non-aqueous solvent has an average LD50, when administered intravenously to a mouse, of greater than or equal to about 2.0 mL/kg.

In another aspect, the invention relates to the composition, wherein the pharmaceutically-acceptable, water-miscible, non-aqueous solvent comprises N-methyl pyrrolidone. In still another aspect, the invention relates to the composition, further comprising a pharmaceutically-acceptable solubilizer. In another aspect, the invention relates to the composition, wherein the pharmaceutically-acceptable solubilizer comprises triacetin or polyethoxylated 12-hydroxy stearic acid. In yet another aspect, the invention relates to the composition, with the proviso that pharmaceutically-acceptable solubilizers are excluded from the composition. In a further aspect, the invention relates to the composition, with the proviso that polyoxyethylated castor oil is excluded from the composition.

In an aspect, the invention relates to a composition made by the acts comprising providing paclitaxel; combining the paclitaxel with a pharmaceutically-acceptable, water-miscible, non-aqueous solvent; wherein the composition is suitable for administration to a host in need thereof, and wherein the composition has a concentration of paclitaxel greater than or equal to about 1.5 mg/mL, a viscosity less than or equal to about 3.0 cp, as determined by the pipette/capillary method, and is substantially stable for four weeks at 50° C.; and wherein the pharmaceutically-acceptable, water-miscible, non-aqueous solvent has an average LD50, when administered intravenously to a mouse, of greater than or equal to about 2.0 mL/kg.

In another aspect, the invention relates to a method of administering paclitaxel to a host in need thereof comprising: providing a composition as disclosed herein; and administering the composition to a host in need thereof. In still another aspect, the invention relates to kits comprising the composition disclosed herein in a pharmaceutically acceptable dosage form.

In another aspect, the invention relates to a composition comprising paclitaxel; and a pharmaceutically-acceptable, water-miscible, non-aqueous solvent; wherein the composition is substantially ethanol-free. In another aspect, the invention relates to the composition, wherein the pharmaceutically-acceptable, water-miscible, non-aqueous solvent comprises N-methyl pyrrolidone, propylene glycol, ethyl acetate, dimethyl sulfoxide, dimethyl acetamide, benzyl alcohol, 2-pyrrolidone, or benzyl benzoate. In yet another aspect, the invention relates to the composition, wherein the pharmaceutically-acceptable, water-miscible, non-aqueous solvent comprises N-methyl pyrrolidone. In still another aspect, the invention relates to the composition, further comprising a pharmaceutically-acceptable solubilizer. In another aspect, the invention relates to the composition, wherein the pharmaceutically-acceptable solubilizer comprises triacetin or polyethoxylated 12-hydroxy stearic acid. In yet another aspect, the invention relates to the composition, with the proviso that pharmaceutically-acceptable solubilizers are excluded from the composition. In a further aspect, the invention relates to the composition, with the proviso that polyoxyethylated castor oil is excluded from the composition.

In another aspect, the invention relates to a composition made by the acts comprising providing paclitaxel; combining the paclitaxel with a pharmaceutically-acceptable, water-miscible, non-aqueous solvent; wherein the composition is substantially ethanol-free. In another aspect, the invention relates to a method of administering paclitaxel to a host in need thereof comprising providing the composition disclosed herein; and administering that composition to a host in need thereof. In another aspect, the invention relates to a kit comprising the composition disclosed herein in a pharmaceutically acceptable dosage form.

In another aspect, the invention relates to a composition comprising paclitaxel; and a pharmaceutically-acceptable, water-miscible, non-aqueous solvent; wherein the composition is substantially ethanol-free. In another aspect, the invention relates to the composition, wherein the pharmaceutically-acceptable, water-miscible, non-aqueous solvent comprises N-methyl pyrrolidone, propylene glycol, ethyl acetate, dimethyl sulfoxide, dimethyl acetamide, benzyl alcohol, 2-pyrrolidone, or benzyl benzoate. In yet another aspect, the invention relates to the composition, wherein the pharmaceutically-acceptable, water-miscible, non-aqueous solvent comprises N-methyl pyrrolidone. In still another aspect, the invention relates to the composition, further comprising a pharmaceutically-acceptable solubilizer. In another aspect, the invention relates to the composition, wherein the pharmaceutically-acceptable solubilizer comprises triacetin or polyethoxylated 12-hydroxy stearic acid. In yet another aspect, the invention relates to the composition, with the proviso that pharmaceutically-acceptable solubilizers are excluded from the composition. In a further aspect, the invention relates to the composition, with the proviso that polyoxyethylated castor oil is excluded from the composition.

In an aspect, the invention relates to a composition made by the acts comprising: providing paclitaxel; combining the paclitaxel with a pharmaceutically-acceptable, water-miscible, non-aqueous solvent; wherein the pharmaceutically-acceptable, water-miscible, non-aqueous solvent comprises N-methol-2-pyrrolidone, 2-pyrrolidone, dimethyl sulfoxide, propylene glycol, benzyl alcohol, ethyl acetate, or dimethylacetamide. In another aspect, the invention relates to a method of administering paclitaxel to a host in need thereof comprising: providing the composition disclosed herein; and administering the composition to a host in need thereof. In a further aspect, the invention relates to a kit comprising the composition in a pharmaceutically acceptable dosage form.

Pharmaceutical grade paclitaxel suitable for use in this invention may be obtained from a variety of sources, including the National Cancer Institute (Bethesda, Md.). In the context of this invention, paclitaxel may be taken to mean paclitaxel proper, and paclitaxel derivatives, analogs, and prodrugs thereof.

Solvents usable in the practice of this invention include pharmaceutically-acceptable, water-miscible, non-aqueous solvents. In the context of this invention, these solvents should be taken to include solvents that are generally acceptable for pharmaceutical use, substantially water-miscible, and substantially non-aqueous. Preferably, these solvents are also non-phthalate plasticizer leaching solvents, so that, when used in medical equipment, they substantially do not leach phthalate plasticizers that may be present in the medical equipment. More preferably, the pharmaceutically-acceptable, water-miscible, non-aqueous solvents usable in the practice of this invention include, but are not limited to, N-methyl pyrrolidone (NMP); propylene glycol; ethyl acetate; dimethyl sulfoxide; dimethyl acetamide; benzyl alcohol; 2-pyrrolidone; benzyl benzoate; $C_{2-6}$ alkanols; 2-ethoxyethanol; alkyl esters such as 2-ethoxyethyl acetate, methyl acetate, ethyl acetate, ethylene glycol diethyl ether, or ethylene glycol dimethyl ether; (s)-(–)-ethyl lactate; acetone; glycerol; alkyl ketones such as methylethyl ketone or dimethyl sulfone; tetrahydrofuran; cyclic alkyl amides such as caprolactam; decylmethylsulfoxide; oleic acid; aromatic amines such as N,N-diethyl-m-toluamide; or 1-dodecylazacycloheptan-2-one.

The most preferred pharmaceutically-acceptable, water-miscible, non-aqueous solvents comprise N-methyl pyrrolidone (NMP), propylene glycol, ethyl acetate, dimethyl sulfoxide, dimethyl acetamide, benzyl alcohol, 2-pyrrolidone, or benzyl benzoate. Ethanol may also be used as a pharmaceutically-acceptable, water-miscible, non-aqueous solvent according to the invention, despite its negative impact on stability. Additionally, triacetin may also be used as a pharmaceutically-acceptable, water-miscible, non-aqueous solvent, as well as functioning as a solubilizer in certain circumstances.

NMP may be available as Pharmasolve® from International Specialty Products (Wayne, N.J.). Benzyl alcohol may be available from J. T. Baker, Inc. Ethanol may be available from Spectrum, Inc. Triacetin may be available from Mallinkrodt, Inc.

Solubilizers may also be used in the practice of this invention. Solubilization is a phenomenon that enables the formation of a solution. It is related to the presence of amphiphiles—those molecules that have the dual properties of being both polar and non-polar—in the solution that have the ability to increase the solubility of materials that are normally insoluble or only slightly soluble, in the dispersion medium. Solubilizers often have surfactant properties. Their function may be to enhance the solubility of a solute in a solution, rather than acting as a solvent, although in exceptional circumstances, a single compound may have both solubilizing and solvent characteristics. Solubilizers useful in the practice of this invention include, but are not limited to, triacetin, polyethylene glycols (such as PEG 300, PEG 400, or their blend with 3350), polysorbates (such as Polysorbate 20, Polysorbate 40, Polysorbate 60, Polysorbate 65, or Polysorbate 80), poloxamers (such as Poloxamer 124, Poloxamer 188, Poloxamer 237, Poloxamer 338, or Poloxamer 407), polyoxyethylene ethers (such as Polyoxyl 2 cetyl ether, Polyoxyl 10 cetyl ether, and Polyoxyl 20 cetyl ether, Polyoxyl 4 lauryl ether, Polyoxyl 23 lauryl ether, Polyoxyl 2 oleyl ether, Polyoxyl 10 oleyl ether, Polyoxyl 20 oleyl ether, Polyoxyl 2 stearyl ether, Polyoxyl 10 stearyl ether, Polyoxyl 20 stearyl ether, Polyoxyl 100 stearyl ether), polyoxylstearates (such as Polyoxyl 30 stearate, Polyoxyl 40 stearate, Polyoxyl 50 stearate, Polyoxyl 100 stearate), polyethoxylated stearates (such as a polyethoxylated 12-hydroxy stearate), and Tributyrin. In a preferable embodiment, pharmaceutically-acceptable solubilizers are excluded from the inventive composition. In another preferable embodiment, polyoxyethylated castor oil is excluded from the inventive composition.

Other materials that may be added to the invention compositions include cyclodextrins, and cyclodextrin analogs and derivatives, and other soluble excipients that could enhance the stability of the inventive composition, maintain the product in solution, or prevent side effects associated with the administration of the inventive composition. Cyclodextrins may be available as Encapsin® from Janssen Pharmaceuticals.

The inventive compositions may be prepared by dissolving paclitaxel in a small quantity of the pharmaceutically-acceptable, water-miscible, non-aqueous solvent with moderate agitation. The volume of the inventive composition is then made up with the remaining solvent and ingredients and mixed thoroughly. In embodiments where the inventive compositions comprise excipients, the excipients, such as hydroxypropyl cyclodextrin, may be dissolved in an aliquot of the pharmaceutically-acceptable, water-miscible, non-aqueous solvent. This aliquot may then be mixed with a premixed solution of paclitaxel and pharmaceutically-acceptable, water-miscible, non-aqueous solvent as described above. The mixed aliquots are then mixed together, and the remaining volume is made up, all under moderate agitation.

The inventive compositions may contain varying amounts of each of the paclitaxel, the pharmaceutically-acceptable, water-miscible, non-aqueous solvent, and other ingredients. In a preferable embodiment, the inventive compositions comprise paclitaxel in an amount ranging from about 0.001 to about 1% w/v, more preferably from about 0.01 to about 0.8% w/v. In another preferable embodiment, the composition comprises paclitaxel in an amount greater than or equal to about 1.5 mg/ml, more preferably in an amount greater than or equal to about 2.5 mg/ml. In still another preferable embodiment, the inventive compositions comprise the pharmaceutically-acceptable, water-miscible, non-aqueous solvent in an amount ranging from about 25% w/v to about 99.999% w/v, more preferably from about 50 to about 99.99% w/v, and still more preferably from about 75 to about 99% w/v. In another preferable embodiment, the inventive compositions comprise a solubilizer in an amount ranging from about 0.001 to about 50% w/v, more preferably from about 0.01 to about 30% w/v. The ratio of w/v in this context refers to the weight of the material divided by the total volume of the solution or formulation.

The inventive compositions may be used in the treatment of a variety of cancers, including, but not limited to ovarian carcinoma, breast carcinoma, lung carcinoma and Kaposi's sarcoma.

The compositions according to the invention may be administered in any medically suitable manner, preferably parenterally or orally, more preferably parenterally, and still more preferably intravenously. The compositions may be diluted with sterile water, normal saline, D5W, Ringer's solution or other equivalent infusion liquids. Preferable dilutions range from about 5:1 to about 1:10 v/v of the inventive composition to the diluting infusion liquids. More preferably, the dilution ranges from about 2:1 to 1:2. Most preferably, the dilution may be 1:1. The ratio of v/v in this context refers to the ratio of the volume of the composition before dilution with the infusion fluids to the total volume of the composition following dilution with the infusion fluid. Additionally, the inventive compositions may be administered in a bolus fashion.

Generally, a therapeutic dose of paclitaxel ranges from about 135 to about 175 mg/m$^2$ of paclitaxel. This dosage may be administered over a range of time from approximately thirty minutes to approximately 24 hours. An advantage of this invention is that relatively little dilution with infusion fluids may need to be made as part of the administration procedure, although larger dilution volumes may be contemplated as within the scope of the invention Conventional pre-medication optionally may be performed before administering the inventive compositions to a patient, to reduce the chance of hypersensitivity reactions. Additionally, desensitization procedures optionally may be performed.

In one embodiment, the inventive compositions are substantially ethanol-free, although various other embodiments of the invention comprise compositions that comprise ethanol. Preferable inventive compositions that are substantially ethanol-free surprisingly and unexpectedly exhibit superior chemical stability of paclitaxel compared to compositions that are not substantially ethanol-free.

Chemical stability generally refers to the amount of chemical degradation of a particular material. Obviously, when administering materials such as paclitaxels, a highly stable formulation is desirable. Chemical stability of a pharmaceutical preparation depends upon the amount of chemical degradation of the active pharmaceutical ingredient in that preparation. Commonly, stability analysis of a pharmaceutical preparation, such as a liquid parenteral product, may be performed under accelerated temperature conditions, such as in a 50° C. oven. The kinetic methods used in the accelerated stability analysis need not involve detailed studies of mechanism of degradation to be able to predict stability, but they are preferably based upon sound scientific principles and compliance with regulatory requirements.

Developing formulations of acceptable chemical stability may be important, especially in cases where the composition comprises a cytotoxic drug like the paclitaxels. Physicians will find undesirable those products for which they must determine the exact amount of paclitaxel present before using the products. Additionally, regulatory requirements may specify minimum stability requirements. Therefore, discovery of variables that impact stability is a useful step in development of new pharmaceutical formulations.

The inventors do not wish to be bound by a particular explanation of the mechanism by which ethanol may be responsible for degradation of paclitaxel, as such explanation is not necessary to practice the invention. It may be, however, helpful to consider some hypothetical mechanisms for possible reasons for paclitaxel degradation in the presence of ethanol. Those pharmaceutical agents that have an ester linkage, such as paclitaxel, can be cleaved by an alcohol, specifically ethanol. The presence of ethanol, therefore may serve to increase the rate of degradation of paclitaxel with concomitant reduction in stability.

Acceptable stability varies from case to case, but is a term reasonably well understood by one of skill to mean chemical stability that is sufficient for the material to be well accepted in clinical use. In a preferred embodiment, the chemical stability of paclitaxel in a 50° C. oven over four weeks is greater than about 85%. In a more preferred embodiment, the chemical stability of paclitaxel in a 50° C. oven over four weeks is greater than about 90%. In a still more preferred embodiment, the chemical stability of paclitaxel in a 50° C. oven over four weeks is greater than about 93%. In a most preferred embodiment, the chemical stability of paclitaxel in a 50° C. oven over four weeks is greater than about 96%.

Another interesting factor in pharmaceutical formulation development is vehicle toxicity. While varying amounts of toxicity are acceptable, especially in cytotoxic formulations, it is nevertheless desirable to reduce vehicle toxicity whenever practical. One surrogate measurement for vehicle toxicity is the LD50—the dosage at which 50% of the test subject die from being administered the vehicle. Common models for LD50 include well-accepted animal models such as the mouse. Mouse intravenous LD50 values can serve to quantify the levels of vehicle toxicity between different vehicles, and serve a useful role in selecting appropriate vehicles for pharmaceutical formulation development. In a preferred embodiment, the pharmaceutically-acceptable, water-miscible, non-aqueous solvents according to the invention have an intravenous LD50 in mice of greater than or equal to about 0.5 ml/kg, more preferably greater than or equal to about 1.5 ml/kg, still more preferably greater than or equal to about 2.0 ml/kg, and most preferably greater than or equal to about 2.5 ml/kg.

Another interesting characteristic of the present invention is that the inventive compositions are of relatively low viscosities, even at high paclitaxel concentrations. This is in contrast to Taxol®, which is of relatively high viscosity at high paclitaxel concentrations. The viscosity of paclitaxel-containing formulation was investigated as follows.

The viscosity of a Newtonian liquid may be determined by measuring the time required for the liquid to pass between two marks as it flows by gravity through a vertical capillary tube. The time of flow of liquid under the test is compared with the time required for a liquid of known viscosity (usually water) to pass between the two marks. If $\eta_1$ and $\eta_2$ are the viscosities of the unknown and the standard liquids, $\rho_1$ and $\rho_2$ are the densities of the liquids, $t_1$ and $t_2$ are the respective flow times in seconds, the absolute viscosity of the unknown liquid, $\eta_{rel}$, is determined by substituting the experimental values in this equation, $$\eta_1/\eta_2 = \rho_1 t_1/\rho_2 t_2 \qquad (1)$$

$$\eta_1/\eta_2 = \eta_{rel} \qquad (2)$$

The equation is based on the Poiseuille's law for a liquid flowing through a capillary tube, $$\eta = \frac{\pi r^4 \Delta P}{8lV} \qquad (3)$$

in which r=radius of the capillary, t=time of flow, $\Delta P$=pressure head in dynes/cm$^2$ under which the liquid flows, l=length of the capillary, and V is the volume of liquid flowing. The radius, length and the volume of the capillary are invariants and may be combined into a constant K. Thus, $$\eta = Kt\Delta P \qquad (4)$$

The pressure head $\Delta P$ depends on the r of the liquid, the acceleration due to gravity, and the height of the liquid of which the latter two parameters are invariant for a given tube, represented by a constant k'. Therefore, the viscosities of the unknown and the standards are as follows, $$\eta_1 = K'\rho_1 t_1 \qquad (5)$$

$$\eta_2 = K'\rho_2 t_2 \qquad (6)$$

The division of (5) by (6) leads to equation (1).

Therefore, measuring the viscosities of various paclitaxel containing formulations is possible. Lower viscosity formulations are generally desirable because of their relative ease of flow and administration. Viscosities may be measured using the pipette/capillary method. In this method, the time of flow for 1 mL of a particular formulation or liquid with unknown viscosity may be measured with a stopwatch using a standard volumetric pipette of constant length, diameter, and volume, such as a 1 mL volumetric pipette. This time of flow may be compared against the time of flow for a liquid of known viscosity to arrive at a viscosity determination for the unknown liquid.

Another interesting aspect of the invention relates to the effect of dilution on the clarity of various paclitaxel containing formulations. As recommended in the Physician's Desk Reference (PDR), the preparation for i.v. adminstration of Taxol® involves dilution prior to infusion. Taxol® may be diluted in 0.9% Sodium Chloride for Injection USP, 5% Dextrose for Injection USP, 5% Dextrose and 0.9% Sodium Chloride for Injection USP, or 5% Dextrose in Ringer's Solution for Injection USP to a final concentration of 0.3–1.2 mg/ml. The solutions may be physically and chemically stable for up to 27 hours at room temperature and room lighting conditions. Taxol® or Taxol® equivalent formulations of paclitaxel containing Cremophor, when diluted 1:3 or 1:4 with 0.9% NaCl to achieve a drug concentration of 0.75 or 0.38 mg/mL, respectively, may remain clear for 24±3 hr. However, those diluted 1:1 or 1:2 with 0.9% NaCl to achieve a drug concentration of 3.0 or 1.5 mg/mL respectively, show signs of precipitation within this time. In contrast, the inventive compositions, when diluted 1:1 to achieve a concentration range of 2.5–4 mg/mL (depending on the cosolvent composition) are able to remain clear for 24±3 hr. In addition, the viscosities of these diluted formulations are comparable to the 1:3 and 1:4 dilutions of the earlier Cremophor containing formulations facilitating intravenous administration. Therefore, the inventive compositions may be diluted to equivalent viscosities of diluted, conventional, Taxol® or Taxol® equivalent formulations, using smaller volumes of diluting infusion fluids. The diluted inventive formulations may have acceptable physical stability for up to 24 hours.

It will be apparent to those skilled in the art that various modifications and variations can be made in the compositions, kits, and methods of the present invention without departing from the spirit or scope of the invention. Thus, it is intended that the present invention cover the modifications and variations of this invention provided they come within the scope of the appended claims and their equivalents. Additionally, the following examples are appended for the purpose of illustrating the claimed invention, and should not be construed so as to limit the scope of the claimed invention.

EXAMPLES

Example 1

Four thousand milligrams of NMP were weighed out in a beaker. An aliquot of the NMP was removed. The aliquot was then combined with ten milligrams of paclitaxel under moderate agitation. This aliquot was then recombined with the remainder of the NMP material, under moderate agitation. The total volume of the recombined mixture was 3.9 mL.

This recombined mixture was then tested for chemical stability of paclitaxel by placing an aliquot of the mixture in a 50° C. stability oven. Samples were taken at one week intervals and tested for chemical stability. The stability testing was performed using an HPLC method. An LC-F (penta-fluorophenyl bonded phase) 5 μm, 100 Å pore size, 4.6×250 mm column was used. A UV detector was used, and set at 227 nm. The mobile phase was made up of a 37:58:5 mixture of ACN:Water:MeOH (containing 1 mL/L of $H_3PO_4$). The flow rate was 1.2 mL/minute. The diluent used was acidic methanol (MeOH containing 0.1% acetic acid). The sample concentration was 0.01 mg/mL. The injection volume was 20 μl. The retention time was 14.5 minutes. The results are shown in Table I below.

Example 2

Four thousand milligrams of ethanol were weighed out in a beaker. An aliquot of the ethanol was removed. The aliquot was then combined with ten milligrams of paclitaxel under moderate agitation. This aliquot was then recombined with the remainder of the ethanol material, under moderate agitation. The total volume of the recombined mixture was 5.1 mL.

This recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 3

Two thousand milligrams of ethanol and two thousand milligrams of NMP were weighed out in a beaker. An aliquot of these solvents was removed. The aliquot was then combined with ten milligrams of paclitaxel under moderate agitation. This aliquot was then recombined with the remainder of the ethanol/NMP material, under moderate agitation. The total volume of the recombined mixture was 4.4 mL.

This recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 4

Two thousand milligrams of NMP and 500 milligrams of triacetin were weighed out in a beaker. An aliquot of this mixture was removed. The aliquot was then combined with ten milligrams of paclitaxel under moderate agitation. This aliquot was then recombined with the remainder of the original mixture, under moderate agitation. The total volume of the recombined mixture was 2.4 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 5

Two thousand milligrams of ethanol and 500 milligrams of triacetin were weighed out in a beaker. An aliquot of this mixture was removed. The aliquot was then combined with ten milligrams of paclitaxel under moderate agitation. This aliquot was then recombined with the remainder of the original mixture, under moderate agitation. The total volume of the recombined mixture was 3.2 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 6

One thousand milligrams of NMP, one thousand milligrams of ethanol, and 500 milligrams of triacetin were weighed out in a beaker. An aliquot of this mixture was removed. The aliquot was then combined with ten milligrams of paclitaxel under moderate agitation. This aliquot was then recombined with the remainder of the original mixture, under moderate agitation. The total volume of the recombined mixture was 2.7 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 7

Two thousand milligrams of NMP and 2000 milligrams of ethanol were weighed out in a beaker. An aliquot of this mixture was removed. The aliquot was then combined with ten milligrams of paclitaxel under moderate agitation. Another aliquot was removed from the beaker and combined with 1000 mg of hydroxypropyl cyclodextrin under moderate agitation. Both of these aliquots were then recombined with the remainder of the original mixture, under moderate agitation. The total volume of the recombined mixture was 5.2 mL.

The recombined mixture was then tested for chemical stability of paclitaxel by placing an aliquot of the mixture in a 50 ° C. stability oven. Chemical stability of the paclitaxel was determined using the method outlined in Example 1. The results are shown in Table I below.

Example 8

Four thousand milligrams of NMP were weighed out in a beaker. An aliquot of the NMP was removed. The aliquot was then combined with ten milligrams of paclitaxel under moderate agitation. Another aliquot was removed from the beaker and combined with 1000 mg of hydroxypropyl cyclodextrin under moderate agitation. Both of these aliquots were then recombined with the remainder of the original mixture, under moderate agitation. The total volume of the recombined mixture was 4.9 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 9

Two thousand milligrams of NMP and 2000 milligrams of benzyl alcohol were weighed out in a beaker. An aliquot of this mixture was removed. The aliquot was then combined with ten milligrams of paclitaxel under moderate agitation. This aliquot was then recombined with the remainder of the original mixture, under moderate agitation. The volume of the recombined mixture was 4.2 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

Example 10

One thousand milligrams of NMP, one thousand milligrams of benzyl alcohol, and 500 milligrams of triacetin were weighed out in a beaker. An aliquot of this mixture was removed. The aliquot was then combined with ten milligrams of paclitaxel under moderate agitation. This aliquot was then recombined with the remainder of the original mixture, under moderate agitation. The total volume of the recombined mixture was 2.4 mL.

The recombined mixture was then tested for chemical stability of paclitaxel by placing an aliquot of the mixture in a 50° C. stability oven. Chemical stability of the paclitaxel was determined using the method outlined in Example 1. The results are shown in Table I below.

TABLE I

Summary report (stability):

| Example No.1 | Ingredients | Paclitaxel stability in % at 50 C. | | | |
|---|---|---|---|---|---|
| | | 1 wk | 2 wk | 3 wk | 4 wk |
| 1 | PCT, NMP | 97.67 | 99.06 | 94.54 | 95.55 |
| 2 | PCT, EtOH | 9.05 | discontinued | | |
| 3 | PCT, NMP, EtOH | 87.92 | 83.45 | 83.14 | 88.45 |
| 4 | PCT, NMP, Triacetin | 102.89 | 102.4 | 99.57 | 104.26 |
| 5 | PCT, EtOH, Triacetin | 51.17 | discontinued | | |
| 6 | PCT, NMP, EtOH, Triacetin | 100.28 | 100.71 | 96.52 | 98.13 |
| 7 | PCT, NMP, EtOH, HPBCD | 89.31 | 90.24 | 83.97 | 84.43 |
| 8 | PCT, NMP, HPBCD | 95.39 | 91.79 | 84.74 | 84.62 |
| 9 | PCT, NMP, Benzyl Alcohol | 98.17 | 97.97 | 97.20 | 96.88 |
| 10 | PCT, NMP, Benzyl Alcohol, Triacetin | 99.47 | 99.28 | 97.18 | 96.28 |

Example 11

Two thousand milligrams of NMP and 500 milligrams of Solutol HS-15 are weighed out in a beaker. An aliquot of this mixture is removed. The aliquot is then combined with ten milligrams of paclitaxel under moderate agitation. This aliquot is then recombined with the remainder of the original mixture, under moderate agitation. The total volume of the recombined mixture is 1.98 mL.

The recombined mixture is then tested for chemical stability of paclitaxel by placing an aliquot of the mixture in a 50° C. stability oven. Chemical stability of the paclitaxel is determined using the method outlined in Example 1.

Example 12

The viscosities of a Taxol® equivalent paclitaxel formulation (including Cremophor®, ethanol and paclitaxel) and of compositions according to the invention were tested at various dilution amounts. The viscosity determinations were performed according to the pipette/capillary method, discussed above, under the assumption that the formulations were Newtonian liquids. The time of flow for 1mL of various diluted formulations with unknown viscosities was measured with a stopwatch using a standard volumetric pipette of constant length, diameter, and volume of 1 mL. Similarly, time taken for water, with a known viscosity of 0.89 cp, to flow through the same tube was recorded.

The viscosity determination was made using Poisuelle's equation:

$$\eta_1/\eta_2 = \rho_1 t_1/\rho_2 t_2,$$

as discussed above, wherein subscript 1—denotes "unknown", subscript 2—denotes "known standard", and $\eta$=viscosity, $\rho$=density, t=time. Water was selected at the standard, giving $\eta_2$=0.89 cp, $\rho_2$=1 g/ml, $t_2$=5.87 sec.

| Formulation | Conc. of drug (mg/ml) | $\eta_1$(cp) |
|---|---|---|
| Formula of Example 9, undiluted | 5.00 | 2.38 |
| Example 9, 2:1 dilution with 0.9% NaCL soln. | 3.75 | 1.95 |
| Example 9, 1:1 dilution with 0.9% NaCL soln. | 2.5 | 1.69 |
| Taxol ® equivalent, undiluted | 6.00 | 11.44 |
| Taxol ® equiv., 1:1 dilution with 0.9% NaCL soln. | 3.00 | 21.86 |
| Taxol ® equiv., 1:2 dilution with 0.9% NaCL soln. | 1.50 | 5.06 |
| Taxol ® equiv., 1:3 dilution with 0.9% NaCL soln. | 0.75 | 2.60 |
| Taxol ® equiv., 1:4 dilution with 0.9% NaCL soln. | 0.38 | 1.96 |

The results are plotted in FIG. 1.

We claim:

1. A composition comprising:

a pharmaceutically-acceptable, water miscible, non-aqueous solvent comprising N-methyl pyrrolidone and excluding dimethylacetamide or dimethylsulfoxide; and paclitaxel in a concentration greater than or equal to about 1.5 mg/ml.

2. The composition of claim 1, wherein the composition has a viscosity of less than or equal to about 3.0 cp, as determined by the pipette/capillary method.

3. The composition of claim 1, wherein the composition is at least 84% stable after incubation for four weeks at 50° C.

4. The composition of claim 1, wherein the composition is suitable for administration to a host.

5. The composition of claim 1, further comprising a pharmaceutically-acceptable solubilizer.

6. The composition of claim 5, wherein the pharmaceutically-acceptable solubilizer comprises triacetin or polyethoxylated 12-hydroxy stearic acid.

7. The composition of claim 1, wherein pharmaceutically-acceptable solubilizers are not included in the composition.

8. The composition of claim 1, wherein polyoxyethylated castor oil is not included in the composition.

9. The composition of claim 1, wherein the composition is in a pharmaceutically acceptable dosage form.

10. A composition, comprising:

a pharmaceutically-acceptable, water miscible, non-aqueous solvent consisting of N-methyl pyrrolidone; and paclitaxel in a concentration greater than or equal to about 1.5 mg/mL.

11. The composition of claim 10, wherein the composition has a viscosity of less than or equal to about 3.0 cp, as determined by the pipette/capillary method.

12. The composition of claim 10, wherein the composition is at least 84% stable for four weeks at 50° C.

13. The composition of claim 10, wherein the composition is suitable for administration to a host.

14. The composition of claim 10, further comprising a pharmaceutically-acceptable solubilizer.

15. The composition of claim 14, wherein the pharmaceutically-acceptable solubilizer comprises triacetin or polyethoxylated 12-hydroxy stearic acid.

16. The composition of claim 10, wherein pharmaceutically-acceptable solubilizers are not included in the composition.

17. The composition of claim 10, wherein polyoxyethylated castor oil is not included in the composition.

18. The composition of claim 10, wherein the composition is in a pharmaceutically acceptable dosage form.

19. A method of forming a composition, comprising:

dissolving paclitaxel in a pharmaceutically-acceptable, water-miscible, non-aqueous solvent comprising N-methyl-pyrrolidone and excluding dimethylacetamide or dimethylsulfoxide to a paclitaxel concentration greater than or equal to about 1.5 mg/mL.

20. The method of claim 19, wherein the pharmaceutically-acceptable, water-miscible, non-aqueous solvent consists of N-methyl pyrrolidone.

21. The method of claim 19, further comprising:

combining a pharmaceutically-acceptable solubilizer with the pharmaceutically-acceptable, water-miscible, non-aqueous solvent after dissolving the paclitaxel.

22. The method of claim 21, wherein the pharmaceutically-acceptable solubilizer comprises triacetin or polyethoxylated 12-hydroxy stearic acid.

23. A method for administering paclitaxel to a host, comprising:

providing a composition having a pharmaceutically-acceptable, water miscible, non-aqueous solvent comprising N-methyl pyrrolidone and excluding dimethylacetamide or dimethylsulfoxide, and paclitaxel in a concentration greater than or equal to about 1.5 mg/mL; and administering the composition to the host.

24. The method of claim 23, wherein the pharmaceutically-acceptable, water-miscible, non-aqueous solvent consists of N-methyl pyrrolidone.

25. The method of claim 23, wherein the composition is in a pharmaceutically acceptable dosage form.

* * * * *